US011065407B2

(12) United States Patent
Gillespie et al.

(10) Patent No.: US 11,065,407 B2
(45) Date of Patent: Jul. 20, 2021

(54) RESUSCITATION BAG

(71) Applicant: Capnia, Inc., Redwood City, CA (US)

(72) Inventors: Constantine Andrew Gillespie, San Carlos, CA (US); Otho Newman Boone, Doylestown, PA (US); Pedro E. De La Serna, San Jose, CA (US); Anthony D. Wondka, San Ramon, CA (US)

(73) Assignee: SOLENO THERAPEUTICS, INC., Redwood City, CA (US)

( * ) Notice: Subject to any disclaimer, the term of this patent is extended or adjusted under 35 U.S.C. 154(b) by 595 days.

(21) Appl. No.: 15/368,328

(22) Filed: Dec. 2, 2016

(65) Prior Publication Data

US 2017/0157348 A1     Jun. 8, 2017

Related U.S. Application Data

(60) Provisional application No. 62/262,721, filed on Dec. 3, 2015.

(51) Int. Cl.
| | |
|---|---|
| *A61M 16/00* | (2006.01) |
| *A61M 16/12* | (2006.01) |
| *A61M 16/06* | (2006.01) |
| *A61M 16/08* | (2006.01) |

(52) U.S. Cl.
CPC .... *A61M 16/0078* (2013.01); *A61M 16/0003* (2014.02); *A61M 16/0075* (2013.01); *A61M 16/06* (2013.01); *A61M 16/0816* (2013.01); *A61M 16/125* (2014.02); *A61M 2202/0208* (2013.01); *A61M 2205/3379* (2013.01); *A61M 2240/00* (2013.01)

(58) Field of Classification Search
CPC .......... A61M 16/0003; A61M 16/0078; A61M 16/0075; A61M 16/125; A61M 16/06; A61M 16/0085; A61M 2202/0208
USPC ...................................... 128/205.14
See application file for complete search history.

(56) References Cited

U.S. PATENT DOCUMENTS

| | | | | |
|---|---|---|---|---|
| 3,009,459 | A * | 11/1961 | Ruben ............... | A61M 16/0084 128/205.13 |
| 5,628,305 | A * | 5/1997 | Melker ............. | A61M 16/0048 128/202.29 |
| 6,253,767 | B1 * | 7/2001 | Mantz ............... | A61M 16/0078 128/205.13 |
| 9,517,316 | B2 * | 12/2016 | Peace ................ | A61M 16/0078 |

(Continued)

*Primary Examiner* — Brandy S Lee
*Assistant Examiner* — Nidah M Hussain
(74) *Attorney, Agent, or Firm* — Cooley LLP

(57) ABSTRACT

Resuscitation apparatuses and methods for assisted ventilation are described herein. The apparatuses may include functional elements that allow the manual delivery of a prescribed volume to an adult or an infant lung. Furthermore, the apparatuses may inform and assure an emergency worker that an appropriate volume is being delivered and therefore lessen the possibility of barotrauma from over-delivery, or ventilatory distress from under-delivery. In some embodiments, the apparatuses include biomechanical and ergonomic functional elements that allow an adult hand to hold it in place during operation, while at the same time, allowing the user to actuate the apparatus to deliver only the necessary amount of volume suitable for an infant lung. In other embodiments, a volume-controlled design is applied to pediatric and adult resuscitation.

10 Claims, 7 Drawing Sheets

(56) References Cited

U.S. PATENT DOCUMENTS

| | | | |
|---|---|---|---|
| 2002/0104531 A1* | 8/2002 | Malone | A61M 15/0016 128/200.23 |
| 2017/0266400 A1* | 9/2017 | McCarthy | A61M 16/203 |
| 2018/0021533 A1* | 1/2018 | Gausche-Hill | A61M 16/20 128/205.14 |

* cited by examiner

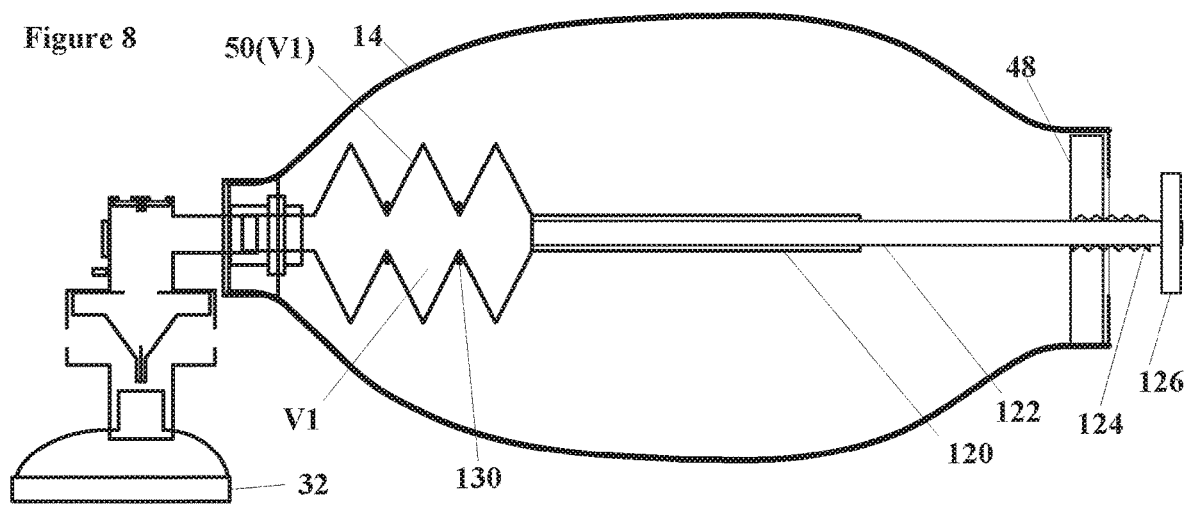
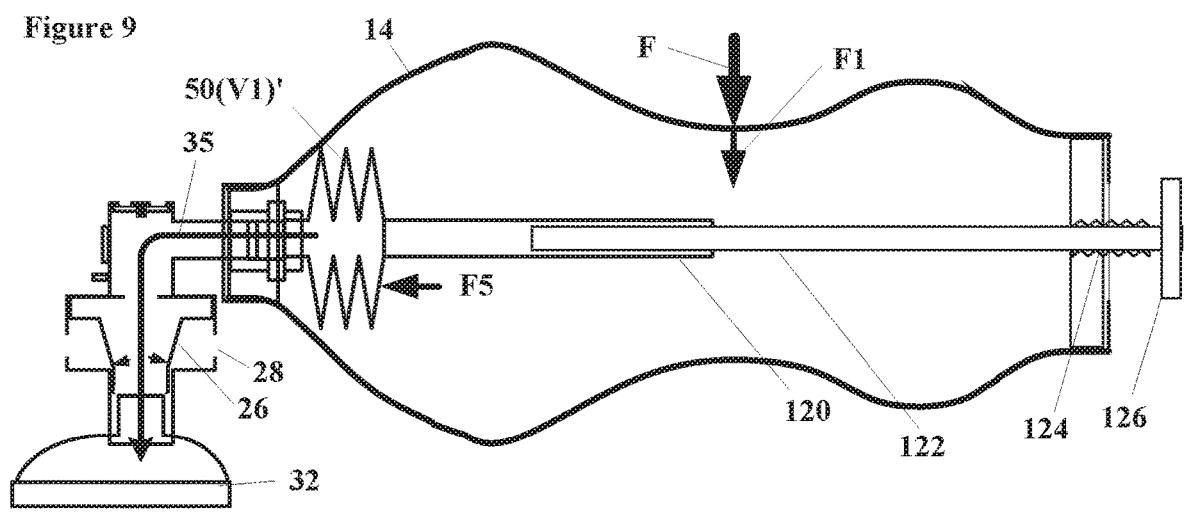
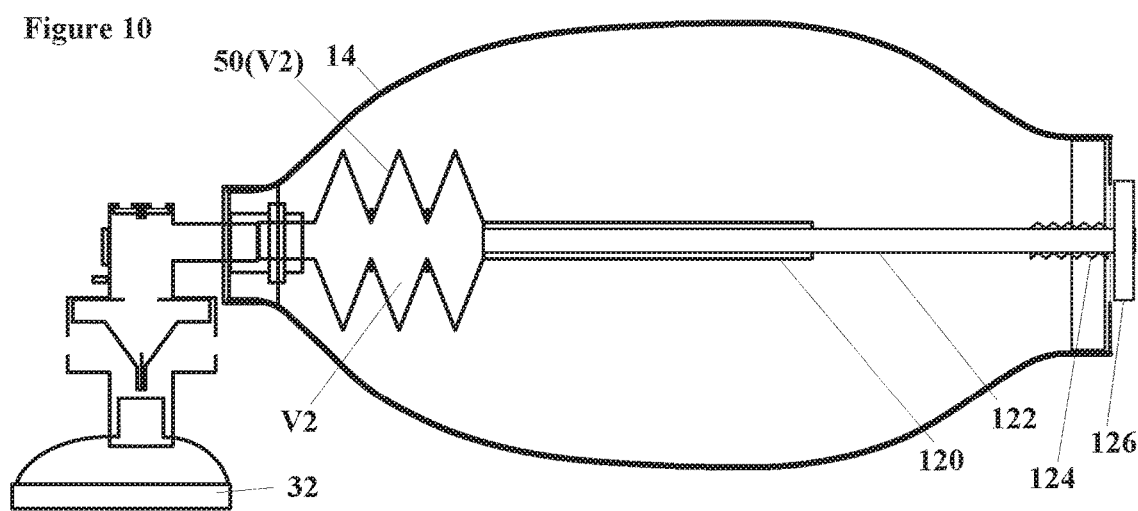

DETAIL A

RESUSCITATION BAG

CROSS-REFERENCE TO RELATED APPLICATIONS

This application claims priority to U.S. Provisional Application No. 62/262,721 filed on Dec. 3, 2015, which is hereby incorporated by reference in its entirety.

FIELD

Described herein are resuscitation apparatuses and methods for assisted ventilation. The apparatuses generally include a first actuator bag, a second ventilation bag, and a volume adjustment mechanism. Delivery of a breath by the resuscitation apparatuses may be accomplished by selecting a breath volume to be delivered and then compressing the first actuator bag, which in turn compresses the second ventilation bag to deliver the selected breath volume to an individual. In this manner, a controlled volume of breath can be delivered.

BACKGROUND

Breathing resuscitation is a common intervention in medicine, for all ages of patients. It is especially common with infants. In the first minutes of extrauterine life, approximately ten percent of newborns require some amount of breathing assistance or breathing resuscitation. Often, a breathing bag with a face mask is used for manual resuscitation, known in the industry as bag-valve-mask (BVM) ventilation. Techniques for BVM ventilation include holding a face mask over the nose and mouth with one hand, while a compliant bag connected to the mask is squeezed with the other hand to force a breath from the bag and through the mask, into the airway and lungs. After delivery of a breath, the bag re-inflates due to the inherent elastic recoil of its material and construction, while the lung passively exhales through the mask via a one way exhalation valve. The bag re-inflates with ambient air through a check valve arrangement. Oxygen can be bled into the bag if necessary to deliver oxygen enriched breaths.

Breaths are delivered at a rate and for a duration typically based on society or institutional guidelines that are communicated and reinforced through training. Instructions for proper technique may for example include: (A) squeezing the bag by an amount so that a rise in the chest wall is seen (indicating a breath is delivered to the lung); and (B) avoiding the delivery of the next breath until the chest is seen to completely recoil, indicating exhalation is complete to avoid breath stacking, which could lead to barotrauma.

Technique, training, and equipment are factors to be considered for providing safe, effective, and reliable manual resuscitation. Serious errors and injury can occur if one or more of these three aspects of resuscitation are insufficient or inadequate. For example, oxygen deprivation caused by inadequate resuscitation may occur, which can lead to brain damage. Further, barotrauma, or over-pressurization of the lung can lead to a tear in the lung wall, and especially the wall of small, fragile infant lungs if too much volume or too much pressure is delivered. Accordingly, specific disadvantages of current BVM ventilation systems are that they fail to deliver a controlled amount of volume to the lung at a controlled or an appropriate pressure. While these current BVM ventilation systems may be equipped with over-pressurization valves, these valves can be slow responding valves and too much pressure or volume can be delivered to the lung before the valve actuates to relieve the excess pressure.

The bags are also typically sized significantly greater than the inspiratory capacity of the patient's lung, especially a child or infant lung, so that they can be grasped adequately by an adult hand. As a result, the user must partially squeeze the bag in order to deliver the correct pressure or volume. Given that the user must estimate how much to squeeze the bag, this type of ventilation is prone to user error. For example, the typical infant bag may include an internal volume of 250 ml, but the user must estimate how much to squeeze the bag so that only 20 ml, or 8% of its volume is displaced so that a breath at a suitable volume and pressure is delivered to the infant.

Given that the skill of BVM ventilation is highly technique dependent, emergency workers are trained using lifelike infant mannequins in order to learn and develop the skill. However, training is infrequent and is generally performed under calm conditions compared to a real emergency event. Brands or styles of BVM resuscitators may thus be changed without workers being retrained with the new brands or styles. Other variables cannot be accounted for in training, such as new resuscitation team members, damaged or missing equipment or equipment pieces, patient variables, and other factors. The stress of the emergency itself can easily lead to incorrect or unsafe resuscitation techniques.

Accordingly, having easier to use and fail-safe resuscitation bags, especially for infants, would be useful. Resuscitation bags that can be used by unskilled personnel would also be useful and help solve an unmet need in regions of the world where the level of medical training is less than in areas with a well-developed heath care infrastructure.

SUMMARY

Described herein are resuscitation apparatuses and methods for delivering a controlled volume of breath to an individual of an adult or pediatric population. For example, the resuscitation apparatuses and methods may be useful in infants. The apparatuses generally comprise a plurality of bags (or containers), where one or more smaller bags may be disposed within the interior of a larger bag. The bags may be structured and sized so that compression of the outer bag results in compression of the one or more inner bags to thereby displace the volume of the one or more inner bags to the individual. A volume adjustment mechanism may be coupled to the one or more inner bags, outer bag, or both, and used to select a prescribed volume of breath, gas, etc., for delivery to the individual. In some variations, the resuscitation apparatus may include a plurality of ventilation bags having different volumes, which are disposed on, or coupled to, the outer surface of a frame. In this variation, the volume adjustment mechanism may be coupled to, or selectively (adjustably) coupled to the plurality of ventilation bags in a manner that selects a particular bag(s) for delivery of a breath. In other variations, the volume adjustment mechanism may be used to adjust or limit the inner bag to the prescribed volume. The outer and inner bags may have any suitable size, shape, geometry, and/or compliance for delivery of a controlled volume to the individual. The outer and inner bags may also be structured for ergonomic use, and in some instances, ease of use with a single hand.

In general, the apparatuses for respiratory resuscitation of an individual include an actuator bag having a non-compressed (resting) state and compressed state; one or more ventilation bags disposed within the actuator bag, where each ventilation bag has a proximal end, a distal end, a first non-compressed (resting) volume, and a second compressed volume; and a volume adjustment mechanism, where the volume adjustment mechanism is configured to select a volume of breath for delivery to the individual, and wherein movement of the actuator bag from its non-compressed (resting) state to its compressed state compresses the one or more ventilation bags to its second compressed volume in order to deliver the selected volume of breath to the individual. In some embodiments, the outer actuator bag is mechanically coupled to the inner ventilation bag.

Alternatively, the apparatuses for respiratory resuscitation of an individual may include a frame; and one or more ventilation bags attached to the frame, where each ventilation bag has an expanded (resting) state and a compressed state, and a predetermined volume of breath, and where compression, i.e., movement from a resting state to a compressed state, of the one or more ventilation bags delivers the predetermined volume of breath to the individual. The frame may be a compliant bag.

The methods described herein are generally used to control the volume of the breath or gas that is delivered to an individual. This may help avoid barotrauma or inadequate resuscitation in infants, as described above. In general, the methods for delivering a controlled volume of breath to an individual include selecting a volume of breath using a volume adjustment mechanism; and compressing an inner ventilation bag by compressing an outer actuator bag, where the inner ventilation bag has a proximal end and a distal end, and compression of the inner ventilation bag delivers the selected volume of breath to the individual.

Alternatively, methods for delivering a controlled volume of breath to an individual may include selecting a volume of breath using a volume adjustment mechanism; and compressing a ventilation bag having the selected volume to deliver the selected volume to the individual. Here the ventilation bag may be coupled to a rotatable volume adjustment mechanism that rotates to fluidly connect the ventilation bag to a manifold (e.g., via a manifold connector) and face mask for delivery of the controlled volume of breath/gas to the individual.

In some embodiments, a resuscitation bag facilitates delivery of a prescribed volume to a patient's lung, especially that of an infant. In some embodiments, the bag can be ergonomically and biomechanically configured to allow it to be reliably and conveniently handled by an adult hand, while at the same time, allowing the user to actuate it to deliver only the necessary desired amount of volume including a relatively small amount of volume suitable for an infant's lung.

In other embodiments, functional elements of the bag, e.g., a volume adjustment mechanism, may allow the user to select or set a particular volume from a choice of volumes, for example, a 10 ml, 15 ml, and 20 ml setting, which generally corresponds to a 2 kg, 3 kg and 4 kg birth weight baby. Additionally or alternatively, the functional element may allow the user to select or set a particular volume of 50 ml, 75 ml, or 100 ml, which may correspond to a 6 month, 12 month, and 18 month old baby. Additionally or alternatively, the functional element may allow the user to select or set a particular volume of 200 ml, 300 ml, or 400 ml, which may correspond to small, medium, and large size adults.

In further embodiments, functional elements of the bag allow the user to set a particular volume from a continuum of settings, for example, anywhere from 10 ml to 30 ml.

In yet further embodiments, functional elements of the bag allow the user to see the amount of volume being delivered to the patient's lung.

In another embodiment, functional elements of the bag allow the user to see the amount of pressure being delivered to the patient's lung.

In further embodiments, an outer bag contains an inner bag, the inner bag in pneumatic communication with a face mask, where the outer bag has a volume between 150 ml and 1 liter.

In further embodiments, an outer bag contains multiple inner bags of different sizes, the inner bags capable of being individually set to be in communication with a face mask.

In further embodiments, a bag may include smaller sacks around the outside of the bag, the sacks capable of being individually set to be in communication with the mask.

In some embodiments, a respiratory resuscitation apparatus for delivering a prescribed amount of gas to an individual may comprise: (1) an outer compliant, substantially hollow and substantially closed structure, the structure adapted to be held with a first hand by an operator; (2) a gas delivery container placed within the outer structure, an end of the container pneumatically coupled to a gas delivery manifold leading to the individual, the remainder of the container closed; and further wherein (i) the outer structure is configured to be squeezed by the first hand of the operator and compress in volume as a result, and (ii) the inner container is configured to reduce in volume in response to a compression of the outer structure.

In some embodiments, a respiratory resuscitation apparatus for delivering a prescribed amount of gas to an individual may comprise: (1) a frame adapted to be held with a first hand of an operator; (2) a gas delivery container placed in conjunction with the frame, an end of the container pneumatically coupled to a gas delivery manifold leading to the individual, the remainder of the container closed; (3) a means to expel the gas in the gas delivery container out of the container and into the manifold; and further wherein the means to expel the gas out of the delivery container is configured to be actuated by the first hand of the operator.

In some embodiments, a respiratory resuscitation apparatus may comprise: an outer container comprising a first interior volume; an inner container comprising a second interior volume, wherein the inner container is disposed within the outer container, and wherein a change in the first interior volume causes a change in the second interior volume.

In further embodiments, the respiratory resuscitation apparatus comprises a mouth piece fluidly coupled to the interior volume, wherein a distance between the mouth piece and the inner container is adjustable.

In further embodiments, the inner container comprises a bellows shape.

In some embodiments, the method for delivering a respiratory gas to an airway of an individual comprises: coupling a respiratory resuscitation apparatus to the airway, the respiratory resuscitation apparatus comprising an outer container and an inner container having a small volume of the respiratory gas; compressing the inner container by compressing the outer container, wherein compressing the inner container delivers the small volume of respiratory gas to the individual.

In further embodiments, the small volume of respiratory gas delivered is about 10 ml, about 15 ml, or about 20 ml.

In further embodiments, the individual is an infant.

BRIEF DESCRIPTION OF THE DRAWINGS

FIG. 8 is a schematic side view of a bag and mask apparatus having another exemplary volume adjustment mechanism, where the mechanism is set to volume V1.

FIG. 9 is a schematic side view of the apparatus shown in FIG. 8 in a compressed state delivering volume V1.

FIG. 10 is a schematic side view of the apparatus shown in FIG. 8, where the volume adjustment mechanism is adjusted to a different volume V2.

DETAILED DESCRIPTION

Described herein are resuscitation apparatuses and methods for delivering a controlled volume of breath to an individual of an adult or pediatric population. For example, the resuscitation apparatuses and methods may be useful in infants. As previously stated, the apparatuses generally comprise a plurality of bags (or containers), where one or more smaller bags may be disposed within the interior of a larger bag. The bags may be structured and sized so that compression of the outer bag results in compression of the one or more inner bags to thereby displace the volume of the one or more inner bags to the individual. A volume adjustment mechanism may be coupled to the one or more inner bags, outer bag, or both, and used to select a prescribed volume of breath, gas, etc., for delivery to the individual. In some variations, the resuscitation apparatus may include a plurality of ventilation bags having different volumes, which are disposed on, or coupled to, the outer surface of a frame. In this variation, the volume adjustment mechanism may be coupled to, or selectively (adjustably) coupled to the plurality of ventilation bags in a manner that selects a particular bag(s) for delivery of a breath. In other variations, the volume adjustment mechanism may be used to adjust or limit the inner bag to the prescribed volume. The outer and inner bags may have any suitable size, shape, geometry, and/or compliance for delivery of a controlled volume to the individual. The outer and inner bags may also be structured for ergonomic use, and in some instances, ease of use with a single hand.

Figure 16:
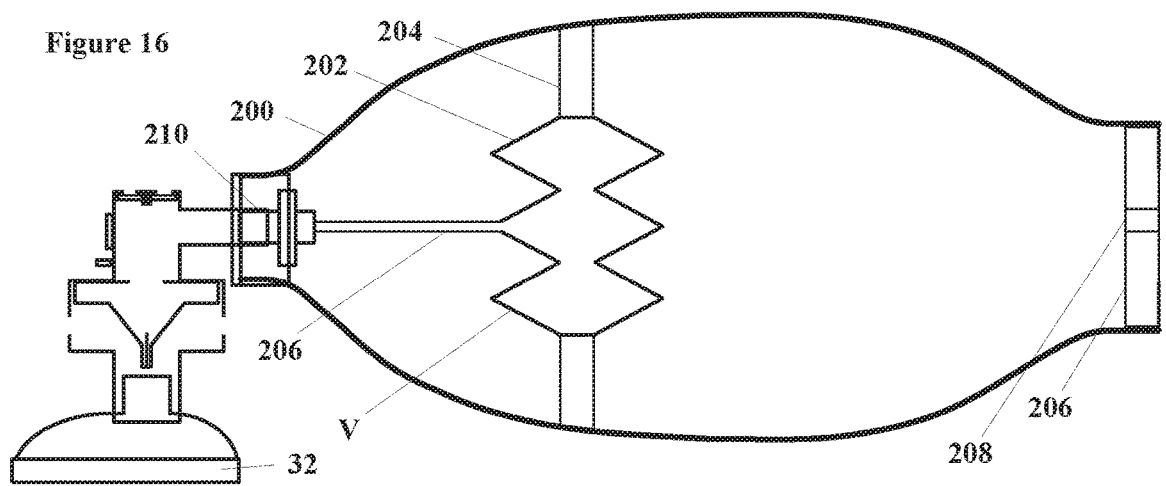
FIG. 16 is a schematic side view of an alternative resuscitation apparatus having an inner compressible structure that can be mechanically compressed by compression of an outer compressible structure.

In some embodiments, the apparatuses for respiratory resuscitation of an individual include an actuator bag having a non-compressed (resting) state and compressed state; one or more ventilation bags disposed within the actuator bag, where each ventilation bag has a proximal end, a distal end, a first non-compressed (resting) volume, and a second compressed volume; and a volume adjustment mechanism, where the volume adjustment mechanism is configured to select a volume of breath for delivery to the individual, and where movement of the actuator bag from its non-compressed (resting) state to its compressed state compresses the one or more ventilation bags to its second compressed volume to deliver the selected volume of breath to the individual. Delivery of the selected volume generally occurs via displacement of the volume in the ventilation bag to the individual by compression of the actuator bag. In some embodiments, the outer actuator bag is mechanically coupled to the inner ventilation bag. An example of such coupling is illustrated in FIG. 16. A mouthpiece may further be coupled to the proximal end of the one or more ventilation bags, and a face mask coupled to the mouthpiece.

The one or more ventilation bags may have any suitable shape, for example, a bellows shape, a conical shape, an oval shape, or a spherical shape. In some instances it may be beneficial for the ventilation bag to have a bellows shape. Furthermore, the ventilation bags and actuator bags may be made from any suitable material. Exemplary materials include without limitation, silicone, polyvinyl chloride, polyethylene, polypropylene, and polyurethane. In some embodiments, the outer actuator bag is made from a transparent material so that compression of an inner ventilation bag can be visualized. Materials for the bags may also be chosen so that the outer bag can be more or less compliant than the inner bag.

The resuscitation apparatuses may include a volume adjustment mechanism for selecting and/or controlling the volume of breath, gas, etc., to the individual. As further described herein, the volume adjustment mechanism may include such components as a guiderail coupled to a flange on one or more of the ventilation bags. The guiderail may include a volume displacement scale.

Alternatively, the volume adjustment mechanism may comprise a slideable spacer at the proximal end of the one or more ventilation bags, or a movable rod or plunger coupled to the distal or proximal end of one or more of the ventilation bags.

In embodiments where the apparatus comprises a plurality of ventilation bags, and each bag has a different volume, the volume adjustment mechanism may include a manifold connector and a ventilation connector, wherein alignment, for example, rotational alignment, of the connectors fluidly connects the ventilation bags to a mouthpiece and/or face mask, to thereby allow delivery of the selected volume to the individual. In yet further embodiments, the volume adjustment mechanism comprises a volume gauge.

The volume of breath that is delivered to the individual being resuscitated may comprise ambient air or oxygen enriched air. When oxygen enriched air is to be delivered, the apparatus may include an air inlet port configured to attach a source of oxygen to the ventilation bag or the actuator bag. The controlled volume of breath may be between about 10 ml to about 100 ml, for example, about 10 ml, about 15 ml, about 20 ml, about 30 ml, about 40 ml, about 50 ml, about 60 ml, about 70 ml, about 80 ml, about 90 ml, or about 100 ml. In some variations, the controlled volume is greater than 100 ml, for example, 150 ml, 200 ml, 250 ml, 300 ml, 350 ml, 400 ml, 450 ml, or 500 ml. It is understood that volume selection may be based on the age and/or size, weight, or other characteristics of the individual. Accordingly, it may be beneficial in an infant to select a volume for delivery of about 10 ml, about 15 ml, or about 20 ml.

Other apparatuses for respiratory resuscitation of an individual may include a frame; and one or more ventilation bags attached to the frame, where each ventilation bag has an expanded (resting) state and a compressed state, and a predetermined volume of breath, and where compression of the one or more ventilation bags delivers the predetermined volume of breath to the individual. In some embodiments, the frame comprises a compliant bag. Here the predetermined volume may be between about 10 ml to about 100 ml, for example, about 10 ml, about 15 ml, about 20 ml, about 30 ml, about 40 ml, about 50 ml, about 60 ml, about 70 ml, about 80 ml, about 90 ml, or about 100 ml. A mouthpiece may further be coupled to the one or more ventilation bags, and a face mask coupled to the mouthpiece. The apparatus may further be configured to include an air inlet port that attaches a source of oxygen to the frame or the one or more ventilation bags.

Methods for delivering a controlled volume of breath to an individual are also described herein, and generally include selecting a volume of breath using a volume adjustment mechanism; and compressing an inner ventilation bag by compressing an outer actuator bag, where the inner ventilation bag has a proximal end and a distal end, and compression of the inner ventilation bag delivers the selected volume of breath to the individual. The individual may be an adult, a child, or an infant.

The selected volume of breath that can be delivered ranges from about 10 ml to about 100 ml. Exemplary volumes include without limitation, 10 ml, about 15 ml, about 20 ml, about 30 ml, about 40 ml, about 50 ml, about 60 ml, about 70 ml, about 80 ml, about 90 ml, and about 100 ml. The selected volume of breath that is delivered may comprise ambient air or oxygen enriched air (supplemental oxygen is delivered with the selected volume of breath).

The ventilation bag from which the controlled volume is delivered may have any suitable shape, for example, a bellows shape, a conical shape, an oval shape, or a spherical shape. In some instances it may be beneficial for the ventilation bag to have a bellows shape. Furthermore, the ventilation bags and actuator bags may be made from any suitable material. Exemplary materials include without limitation silicone, polyvinyl chloride, polyethylene, polypropylene, and polyurethane. In some embodiments, the outer actuator bag is made from a transparent material so that compression of an inner ventilation bag can be visualized. Materials for the bags may also be chosen so that the outer bag can be more or less compliant than the inner bag.

The volume of breath, gas, etc., that is delivered for resuscitation can be controlled or selected with a volume adjustment mechanism. The volume adjustment mechanism can be an element that is slideably advanced or withdrawn, or rotated to select the volume of breath for delivery, or involve rotation of components with respect to one another to select the volume of breath for delivery.

The volume adjustment mechanism may include such components as a guiderail coupled to a flange on one or more of the ventilation bags. The guiderail may include a volume displacement scale. Alternatively, the volume adjustment mechanism may comprises a slideable spacer at the proximal end of the one or more ventilation bags, or a movable rod or plunger coupled to the distal or proximal end of one or more of the ventilation bags.

In embodiments where the apparatus comprises a plurality of ventilation bags, and each bag has a different volume, the volume adjustment mechanism may include a manifold connector and a ventilation connector, wherein alignment, for example, rotational alignment, of the connectors fluidly connects the ventilation bags to a mouthpiece and/or face mask, to thereby allow delivery of the selected volume to the individual. In yet further embodiments, the volume adjustment mechanism comprises a volume gauge.

The volume-limited ventilation bags or containers described herein can solve the conventional problems related to the safe delivery of the needed volume or pressure to patient's lung during emergency resuscitation, especially an infant's lung. In some embodiments, one or more of the following features are included in a ventilation bag: (1) a volume delivery mechanism that is sized to match the lung so that a prescribed desired volume is delivered in a fail-safe manner, (2) a larger adult-hand-sized frame upon which the smaller volume delivery mechanism is disposed, (3) a smaller volume delivery mechanism and larger frame for adult biomechanics such that the frame can be easily and reliably held correctly while at the same time using the same hand holding the frame to deliver the volume required including the miniscule levels of volume required in the case of ventilating an infant. Embodiments described herein may improve the state of the art by allowing (1) setting or selecting of a prescribed desired delivered volume that is to be delivered, based on the patient's size and need, (2) measuring the volume being delivered for an information feedback loop to the operator, (3) measuring the pressure being delivered for an information feedback loop to the operator. These significant improvements over state-of-the-art conventional infant manual resuscitation may advantageously reduce complications related to emergency infant resuscitation, namely oxygen deprivation and barotrauma. The improvements may accomplish this goal by making the equipment easier to reliably use, and by making training easier and less critical, and reducing human error during the stressful emergency situation.

Figure 1:
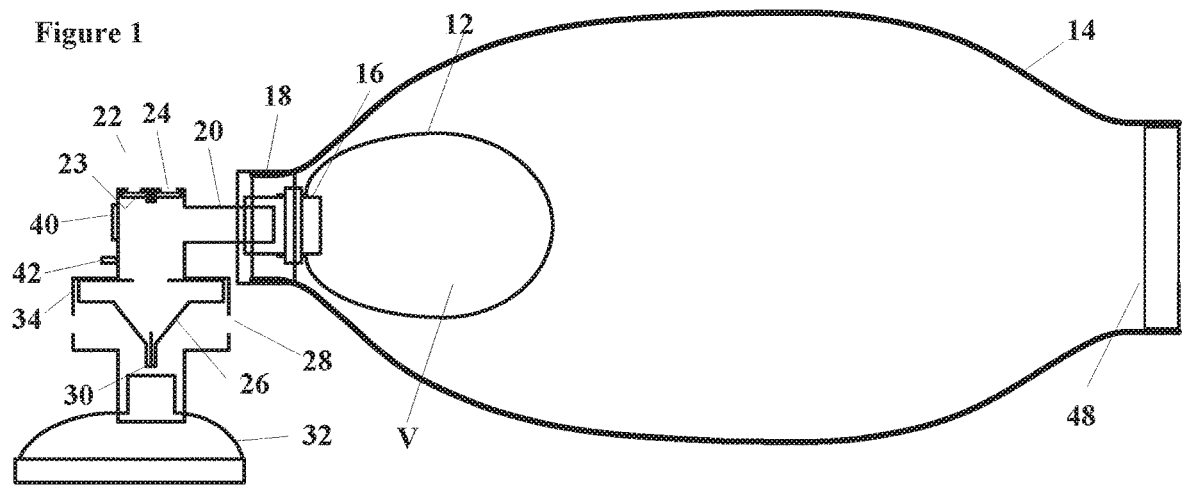
FIG. 1 is a schematic side view of a bag and mask apparatus, showing a compressible ventilation bag in its non-compressed (resting) state within an outer compression actuator bag (also in its resting state), in accordance with an embodiment.

The resuscitation bags may include a smaller inner bag surrounded by a larger outer bag. Both bags may be compressible and configured in a manner where compression of the outer bag results in compression of the inner bag. For example, in FIG. 1, an embodiment of an infant resuscitation bag is shown in a side hidden line view. Ventilation bag 12 is disposed within a larger actuator bag 14. Both bags are compressible and have shape memory such that when not compressed they naturally spring back to their full size (resting, non-compressed state), which is shown in FIG. 1. As will be seen in the subsequent figures, the inner and outer bags generally work in unison to deliver a prescribed volume to an individual, for example, an infant. The actuator bag 14 at the patient (individual) end is connected to a manifold 20 using a collar 18 and creates a fluidic seal with the outer surface of the manifold 20. The inner ventilation bag 12 is connected to the internal flow channel of the manifold 20 with an adaptor 16, thus allowing the volume V within the ventilation bag to communicate with the internal channel of the manifold and ultimately the mask 32. At the patient end of the manifold 20, a ventilation mask 32 is connected. Additional features include a one-way refill valve 22 that may include a diaphragm 23 that seals an inlet port 24, an over-pressure relief valve 40, a supplemental oxygen inlet connector 42, a one-way inspiratory valve 26, which may be a duck bill valve with an opening 30 that is normally closed, an inspiratory valve manifold 34 which houses the inspiratory valve, and an expiratory valve 28. An oxygen reservoir (not shown) may be coupled to the oxygen inlet connector and an oxygen source connected to the reservoir. The actuator bag 14 may include an end cap 48 at the end opposite to the patient. The end cap 48 may include inlet and outlet ports (not shown) configured to create the desired compression and recoil characteristics of the actuator bag 14. The end cap 48 may also be configured to help facilitate assembly of the apparatus and access to and maintenance of the inner ventilation bag 12. Furthermore, the end cap 48 may include a connector that attaches a medical gas reservoir to the inner ventilation bag (not shown).

Figure 2:
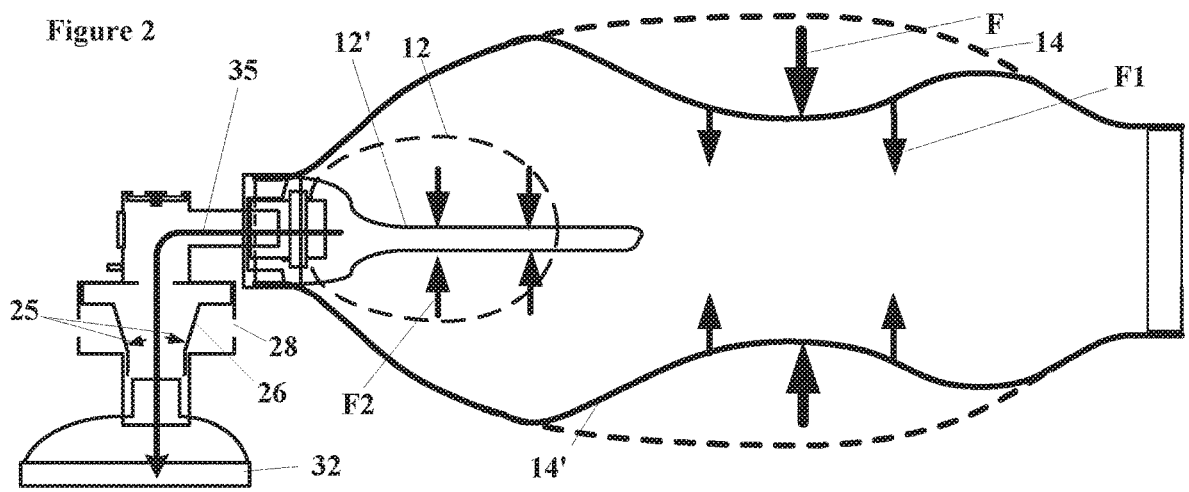
FIG. 2 is a schematic side view of the apparatus of FIG. 1, shown to be delivering a manual breath when the inner ventilation bag is in the compressed state.

In FIG. 2, the inspiratory phase of the resuscitation procedure is shown. The actuator bag 14 is compressed as shown by arrow F to a compressed state 14' by the operator, which thereby creates an internal pressure of F1 inside the actuator bag, which in turn causes the inner ventilation bag 12 to compress F2 from its natural inflated state (resting state) of volume V (FIG. 1) to a compressed state 12', thereby displacing all or some of volume V from the ventilation bag to the mask and patient, as shown by gas flow arrow 35. Because the inner bag is compressible, the outer actuator bag is mechanically permitted by design to compress by at least the volume of the inner bag, due to the laws of gas displacement. Because air is compressible, the outer actuator bag can be compressed by a volume greater than the volume V defined by the inner ventilation bag. Regardless, movement of the outer bag from its non-compressed (resting) state to its compressed state compresses the inner bag so that its volume is displaced and delivered to the individual. In some embodiments, the outer actuator bag is transparent or translucent, so that compression of the inner ventilation bag can be visually confirmed. The flow of gas shown by the small arrows 25 toward the patient opens the low cracking pressure inspiratory valve 26, which closes the expiratory valve 28, allowing the gas from the ventilation bag to be successfully delivered to the patient through the face mask 32.

Figure 3:
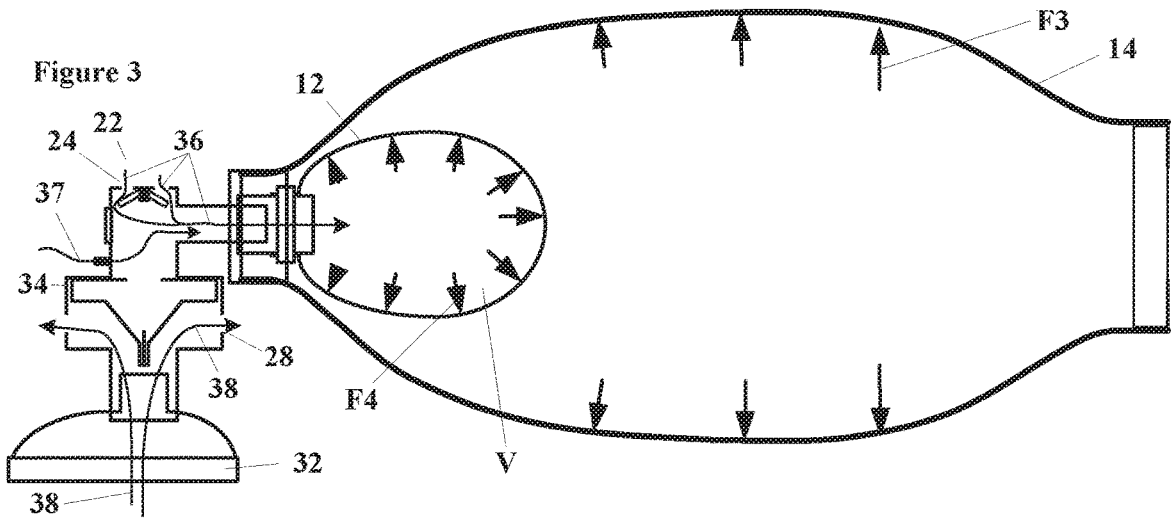
FIG. 3 is a schematic side view of the apparatus of FIG. 1, shown in the recoil state, in which the compression actuator bag recoils to its resting state and the ventilation bag is refilled.

In FIG. 3, the expiratory phase of the resuscitation procedure is shown. Both the actuator bag 14 and the ventilation bag 12 can be resilient and comprise memory material such that when the compressive force F on the actuator bag is removed, both the actuator bag 14 and ventilation bag 12 spring back to their resting (non-compressed) states, as shown in FIG. 1. In some embodiments, the ventilation bag may spontaneously re-inflate by virtue of the recoil force F3 of the actuator bag alone. In other embodiments, the ventilation bag may re-inflate due to its intrinsic recoil properties. When the ventilation bag 12 re-inflates, it may do so with ambient air 36 drawn in through the inlet ports 24 of the re-inflation valve 22. Supplemental oxygen 37 can also be drawn in through the supplemental oxygen connector 42 and an oxygen source (not shown), into the ventilation bag 12. The amount of oxygen drawn in can be regulated to accomplish a desired fractional inspired oxygen (FIO2) such as through a demand valve system or regulator or blender. Also during this phase of resuscitation, the inspiratory valve 34 can be closed and exhaled air 38 from the patient expelled through the open ports of the exhalation valve 28. The compliance or elasticity of the ventilation bag 12 is such that its recoil force F4 to the inflated (non-compressed, resting) state overcomes the cracking pressure of the re-inflation valve 22. The airflow resistance of the expiratory valve 28 is low enough such that it allows the lungs (e.g., an infant's lungs) to passively exhale through the mask 32 and through the valve 28. In an optional embodiment (not shown) the exhalation valve may include a positive end-expiratory pressure (PEEP) valve so that areas of the lungs do not collapse in between inspiratory cycles, and to help recruit all areas of the lungs for maximum ventilation and perfusion. The PEEP valve is used in unison with the expiratory valve 28 to increase the resistance of the valve in a controlled manner, to create the desired amount of PEEP.

As an alternative to the inner ventilation bag shown in FIGS. 1-3, FIG. 4 shows a bellows shaped inner ventilation bag 50 inside the actuator bag 14. This style bag contracts when the outer actuator bag is compressed, and expands to a natural resting state of volume V when the outer actuator bag is not compressed. This configuration may have the advantage of a geometrically more controlled compression, and therefore further insuring the proper volume delivery to the patient. In addition, the user can potentially more easily see the full compression of this style bag compared to other styles. However, it should be noted that while an oval shaped bag 12 (shown in FIG. 1) and a bellows style bag 50 (shown in FIG. 4) are shown in the figures, these ventilation bag configurations are exemplary only, and any shape and style bag or deflate-able/compressible chamber or structure can be used. FIG. 5 shows the bag of FIG. 4 when compressed. The actuator bag 14 is compressed by external force F to a compressive state 14', generating an internal pressure F1, which in turn actuates the inner ventilation bellows 50 with a force F5 to a compressed state 50' thereby expelling some or all of its internal volume V as inspiratory flow 35, opening the inspiratory valve 26, closing the expiratory valve 28, and through the mask 32 and to the patient. As mentioned previously, the bellows can be visualized through the actuator bag, and optionally a scale can be provided (not shown) which could indicate to the user the amount of volume being displaced out of the ventilation bellows.

Figure 4:
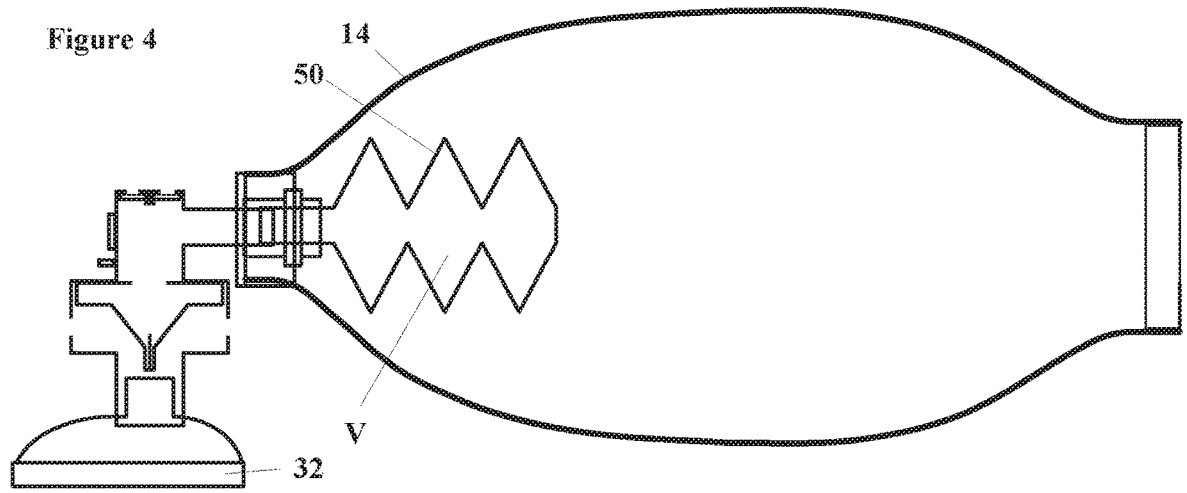
FIG. 4 is a schematic side view of a bag and mask apparatus according to another embodiment, in which a compressible bag inside an outer bag has a bellows or accordion configuration.
Figure 5:
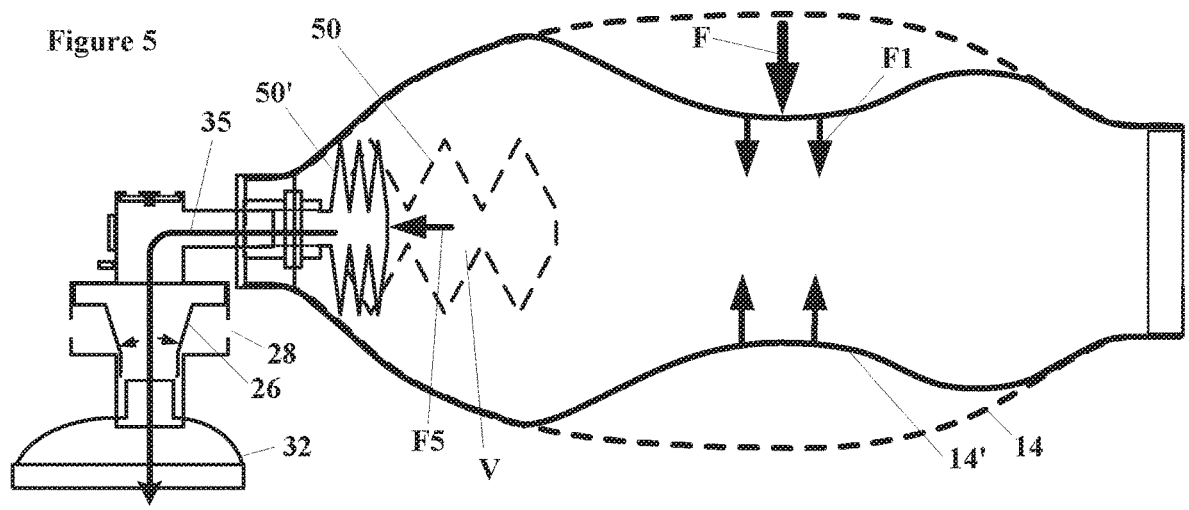
FIG. 5 is a schematic side view of the apparatus of FIG. 4, shown in its compressed state delivering a manual breath that exits the apparatus.
Figure 6:
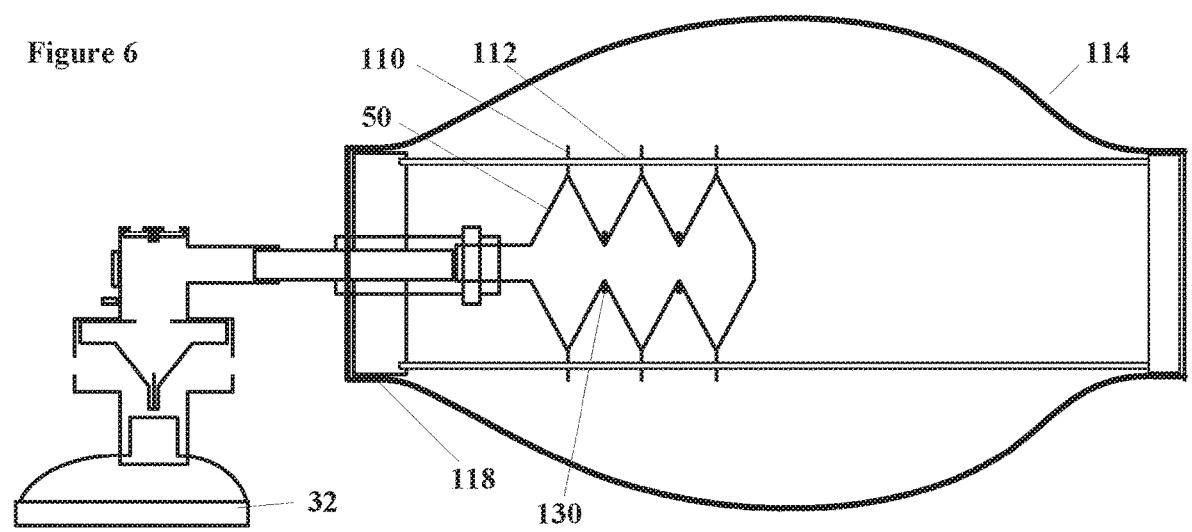
FIG. 6 is a schematic side view of a bag and mask apparatus according to another embodiment having an exemplary volume adjustment mechanism in the form of a compressible bellows that moves along a guideway.

FIG. 6 shows an alternative embodiment of FIG. 4 in which the ventilation bellows 50, inside an alternative actuator bag 114 with alternative collar 118, includes a flange area 110 which includes a guideway for a guiderail 112. The guiderail 112 allows the bellows 50 to compress and expand in a geometrically controlled progression, and may also provide a volume displacement scale (not shown). Also shown in FIG. 6 is a ventilation bellows ring 130 which is placed around the small diameter sections of the bellows

(50) to help the bellows maintain its structure and expand and contract in a controlled geometrical progression.

It should be noted that the actuator bags shown in the figures are designed to be ergonomically, and with proper biomechanics, grasped by an adult. While the bags are shown in a very basic shape, all possible ergonomic shapes can be used, including oval shapes, spherical shapes, cylindrical shapes, tapered shapes, conical shapes, wishbone shapes, and other shapes. The main criteria of the shape is that it shall be a shape that can be ergonomically, and with proper biomechanics, grasped by an adult, and by either hand, and easily and forcefully compressed by one hand.

In some embodiments, additional features are present in the resuscitation apparatuses. The pneumatic pathway (ventilation pathway) between the volume delivery mechanism (i.e., the ventilation bag, sack, or plunger, etc.) and the patient interface (i.e., face mask or airway device) comprises a cross section and volume that is minimized such that when the volume delivery mechanism is actuated, the bolus of breath/gas that is delivered into and out of the face mask to the patient is substantially fresh ambient air, and only a small amount of any rebreathed air. As long as the exhalation valve (see, e.g., FIG. 1, element 28) is positioned and configured correctly, each stroke of the volume delivery mechanism should displace a volume of gas equivalent to the stroke volume through the system and into the patient interface, and then into the patient's airway. Thus, even if the manifold volume between the delivery mechanism and the mask is larger than the volume in the delivery mechanism, the mechanical stroke should deliver fresh gas to the patient interface. Nonetheless, minimal dead space can make the system dynamically more predictable and allow for better control of the flow rate of the delivered inspiratory gas.

In some cases it may be clinically advantageous for the manual breath being delivered by the resuscitation bag to be delivered at a certain flow rate, in order to more effectively inflate the lung and to achieve a desired minute volume over the course of time. In such embodiments, the compliant properties of the ventilation bag can regulate the inspiratory flow rate. The outer bag can be compressed quickly, but the internal ventilation bag will compress in response at a rate regulated by its compliance. Alternatively the outer actuator bag can include features to indicate how much it is being compressed and at which velocity. The features may be visual features, audible features, or both. The compression can produce an audible indicator which is compression rate dependent, to make sure the inspiratory flow rate is correct, for example, a pneumatic sound is produced only when the desired flow rate is correct.

Figure 7:
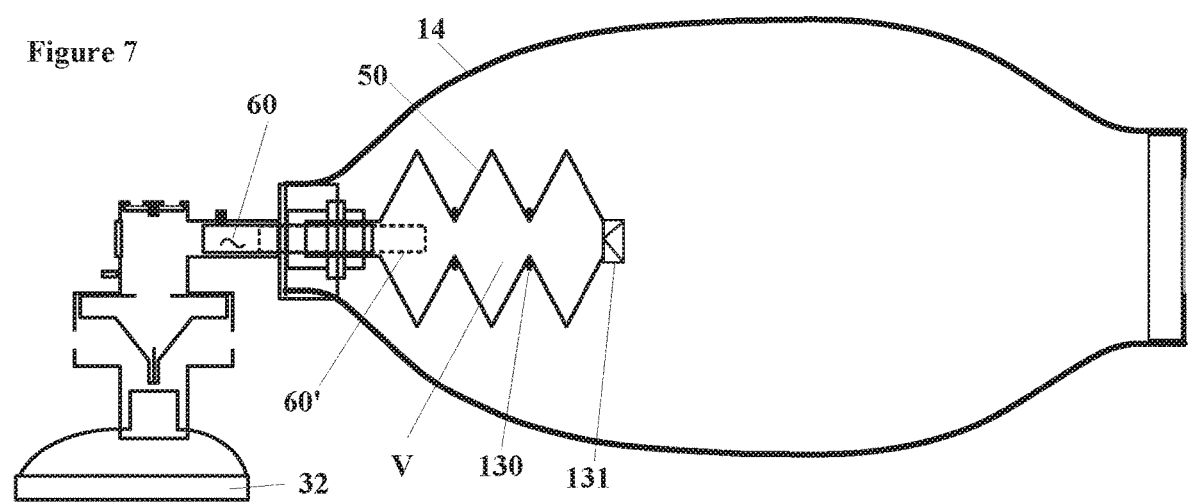
FIG. 7 is a schematic side view of a variant of the apparatus shown in FIG. 6, having features to adjust the volume delivered by the compressible ventilation bag, in accordance with another embodiment.

Now referring to FIG. 7, an alternative embodiment is shown. The resuscitation apparatus in this figure includes an inspiratory volume adjustment which is accomplished by a spacer 60. The spacer 60 can be slid (i.e., advanced and/or and retracted/withdrawn) in and out of the inner ventilation bag 50 to varying depths to thereby alter the inner volume of the inner ventilation bag from a maximum volume V to a lesser volume. A smaller volume setting is shown when the spacer is slid to position 60'. The linear back and forth adjustment or movement of the spacer 60 can be produced by a rotational or a non-rotational mechanism. The spacer 60 is typically positioned inside the flow channel of the manifold, and access to the spacer 60 to move it is done without compromising the fluidic seal of the manifold to the outside ambient surroundings. Alternatively, the spacer 60 can be moved in and out of the inner ventilation bag by movement or rotation of the outer actuator bag 14. Other volume adjustment mechanisms are contemplated. In some embodiments, a mechanism allows for altering the volume of the inner ventilation bag in a controlled, precise fashion and by a known amount. Additionally or alternatively, the ventilation bag or bellows may also include its own pressure relief valve, for example, pressure relief valve 131, which may optionally be adjustable, in order to control the pressure delivered to the patient with extra fidelity.

In FIGS. 8-10, another volume adjustment mechanism is described. In FIG. 8 it can be seen that the inner ventilation bellows 50(V1) with an internal volume V1 includes a guide tube 120. A volume adjustment arm 122 passing through the actuator bag end cap 48 is move-ably inserted into the guide tube, butting up against the end of the bellows 50(V1). The other end of the adjustment arm includes an adjustment knob 126 which when rotated or moved, moves the adjustment arm 122 back and forth accordingly. The linear back and forth movement may be made by rotational means with a thread arrangement 124, or by other means or by non-rotational means. FIG. 9 shows the ventilation bag in FIG. 8 during a compression stroke. The actuator bag 14 is compressed with an external force F, generating an internal pressure of force F1, which cases the ventilation bellows to compress with force F5 from its resting volume V1 and resting state 50(V1) to its compressed state 50(V1)', expelling all or some of volume V1 as inspiratory flow 35. Now referring to FIG. 10, the ventilation bellows is set to a different volume, V2, and resting state 50V2) by adjustment of the adjustment arm 122. Now the ventilation bag is set to deliver volume V2 rather than volume V1 shown in FIGS. 8 and 9. The adjustment knob 126 and endcap 28 may include features to indicate to the user the volume setting of the ventilation bellows. This volume adjustment is exemplary, and the resuscitation apparatuses described herein contemplate all manners in which to adjust the volume of the inner ventilation member or to adjust the amount of compression.

Figure 11:
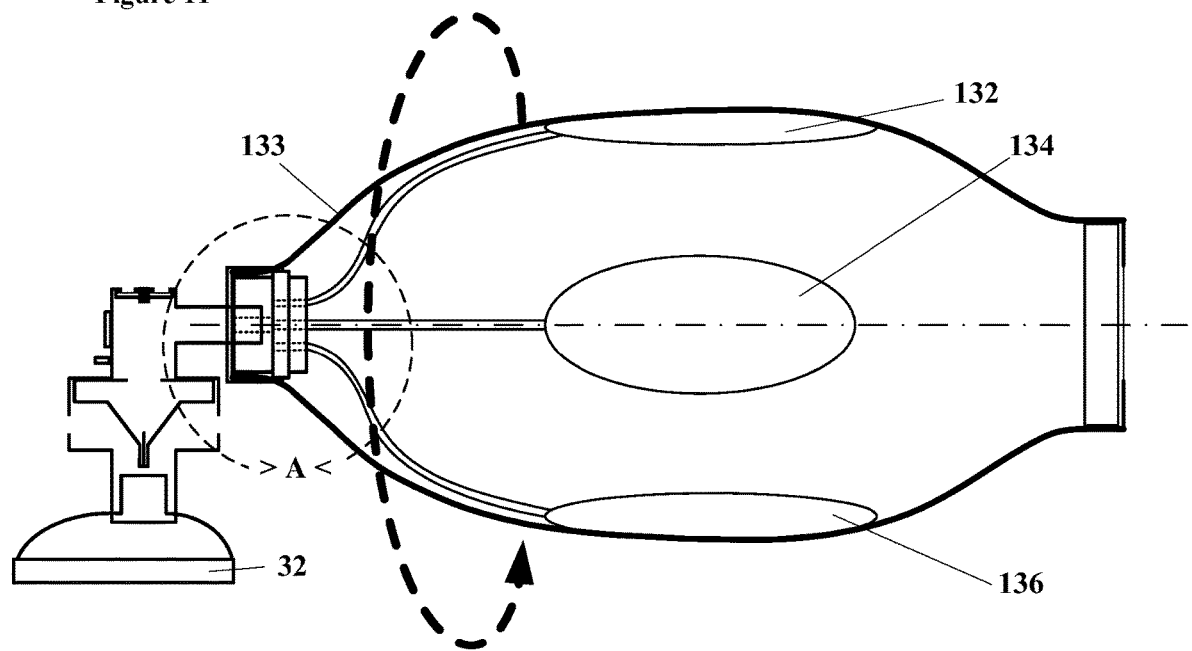
FIG. 11 is a schematic side view of a bag and mask with multiple internal compressible bags of differing volumes and a selection mechanism (volume adjustment mechanism) for selecting which internal bag is pneumatically coupled to the face mask.
Figure 12:
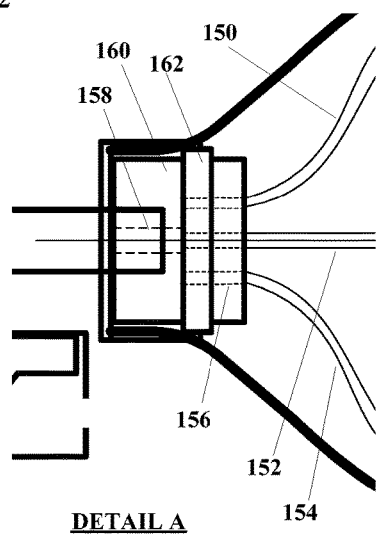
FIG. 12 is a detailed view of the bag-mask pneumatic coupling of FIG. 11.

FIG. 11 shows an alternative resuscitation bag that achieves volume limited delivery and volume delivery adjustment. Multiple internal ventilation bags, 132, 134, 136, are placed inside an outer actuation bag 133. The ventilation bags are compliant with elastic recoil as explained with earlier embodiments. Each bag may be of a different internal volume, for example, 15 ml, 20 ml and 25 ml. When the actuation bag 133 is compressed, a ventilation bag is in turn compressed because of the increase in pressure inside the actuation bag. The exact ventilation bag which is in pneumatic (fluid) communication with the face mask via the gas delivery manifold between the actuation bag and the face mask, can be selected. The selection for example can be performed by rotation of the actuation bag as indicated by the rotation arrow in FIG. 11. FIG. 12 shows detail A of FIG. 11 to show the pneumatic pathway in more detail. The ventilation bags are pneumatically (fluidly) coupled to channels 156 inside a frame connector 162 with connecting tubes 150, 152 and 154. Rotation of the actuation bag 133 rotates the frame/ventilation connector 162 about manifold connector 160 to align and pneumatically (fluidly) couple the ventilation sack channel 156 in the frame/ventilation connector 162 to the gas flow channel 158 in the manifold connector 160. In FIGS. 11 and 12 the apparatus is set to ventilation bag 134 so that the volume of bag 134 is expelled to the patient during actuation.

Figure 13:
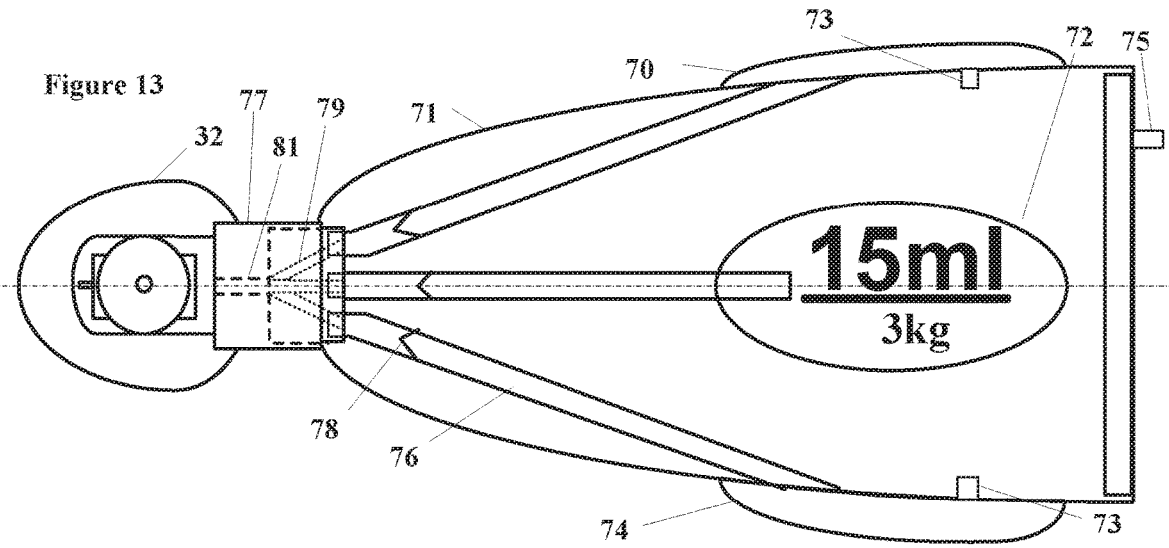
FIG. 13 is a schematic top view of a bag showing compressible ventilation bags of different volumes positioned on a superstructure (frame) that is used as a handle, in accordance with another embodiment, and a volume adjustment mechanism to select which bag is pneumatically coupled to the face mask.

FIG. 13 shows an alternative configuration of the apparatus in which a plurality of ventilation sacks 70, 72, and 74 are placed substantially on the outside of a frame 71. The ventilation sacks are pneumatically (fluidly) connected to a manifold 77 and ultimately the face mask 32 through low dead space flow channels 76, which may include one way valves 78 such that air can be directed only out of the ventilation sacks through the flow channels. Ventilation gas flow to the patient is from the ventilation sack through the flow channels 76, through the channels 79 in the manifold 77, through the channel 81 in the manifold 77 and then through the remainder of the apparatus and through the face mask 32. Re-inflation valves 73 may be placed in the ventilation sacks, which may be re-inflated from the surrounding ambient air outside of the sacks, or by air from inside the frame, which may include oxygen enriched air, enriched to a desired fractional inspired oxygen (FIO2), which is replenished into the frame from an air inlet port 75. In this embodiment, the emergency worker has more than one volume option to use, without worrying about making an adjustment to the apparatus. Each ventilation sack volume option may be clearly marked, for example sack 72 is a 15 ml volume sack that when used, will deliver all or some of 15 ml of volume to the infant which is ideal for a 3 kg infant. The frame 71 in this embodiment is configured to be ergonomically held and enable proper biomechanics, like the actuator bag in the previous figures, while facilitating compression of one of the ventilation sacks by the same hand holding the frame. For example, the palm of the hand may be placed over the sack while the fingers grasping the smaller section of the frame. Or, the ventilation sacks and frame may be configured so that it is the thumb which compresses a ventilation sack. The ventilation sacks and frame can be configured so that only one ventilation sack is compressed at once. The frame may be completely rigid and unyielding to compression when a ventilation sack is compressed, or may be semi-rigid or compliant such that it gives when a ventilation sack is compressed, in order to facilitate complete ventilation sack compression. In the latter case the compliance of the frame is more resilient than that of the sack, so that the sack can be completely compressed. Optionally, the apparatus may comprise only one ventilation sack as an alternative to the way of compressing the ventilation bag shown in FIG. 1. In this case, volume selection and/or volume adjustment if desired can be accomplished by other means described elsewhere herein.

Figure 14:
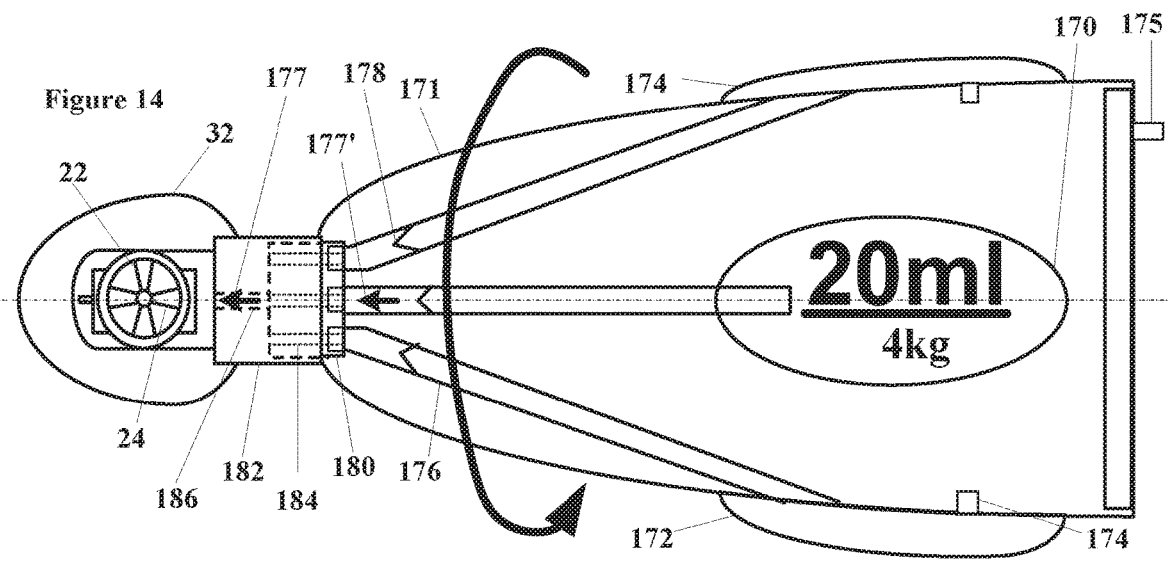
FIG. 14 is a schematic top view of the apparatus shown in FIG. 13 when the apparatus is set to a different volume.

In FIG. 14 an alternative embodiment to that shown in FIG. 13 is described. In this case, one of the ventilation sacks, 170, 172 or 174, is selected to be the ventilation sack to compress. Selection can be accomplished by rotating the frame 171, as shown by the large arrow, to align the desired ventilation sack position denoted by the label 177' with the alignment arrow 177. In the Figure shown, a ventilation sack prominently labeled 20 ml is aligned with the alignment arrow 177, so that compression of the 20 ml ventilation sack will expel all or some of 20 ml, ideal for resuscitation of a 4 kg patient. The ventilation sacks are pneumatically (fluidly) coupled to ventilation sack channels 184 inside a frame connector 182 with connecting tubes 176. Here the volume adjustment mechanism comprises rotation of the frame 171, which rotates the frame connector 180 about manifold connector 182 to align and pneumatically (fluidly) couple the ventilation sack channel 184 inside the frame connector 180 to a gas flow channel 186 inside the manifold connector 182. Re-inflation of the ventilation sacks can be accomplished through a main refill valve 22 in which case the one-way valves 178 would not be included, or through ventilation sack refill valves 173, or both, as described elsewhere herein.

Figure 15:
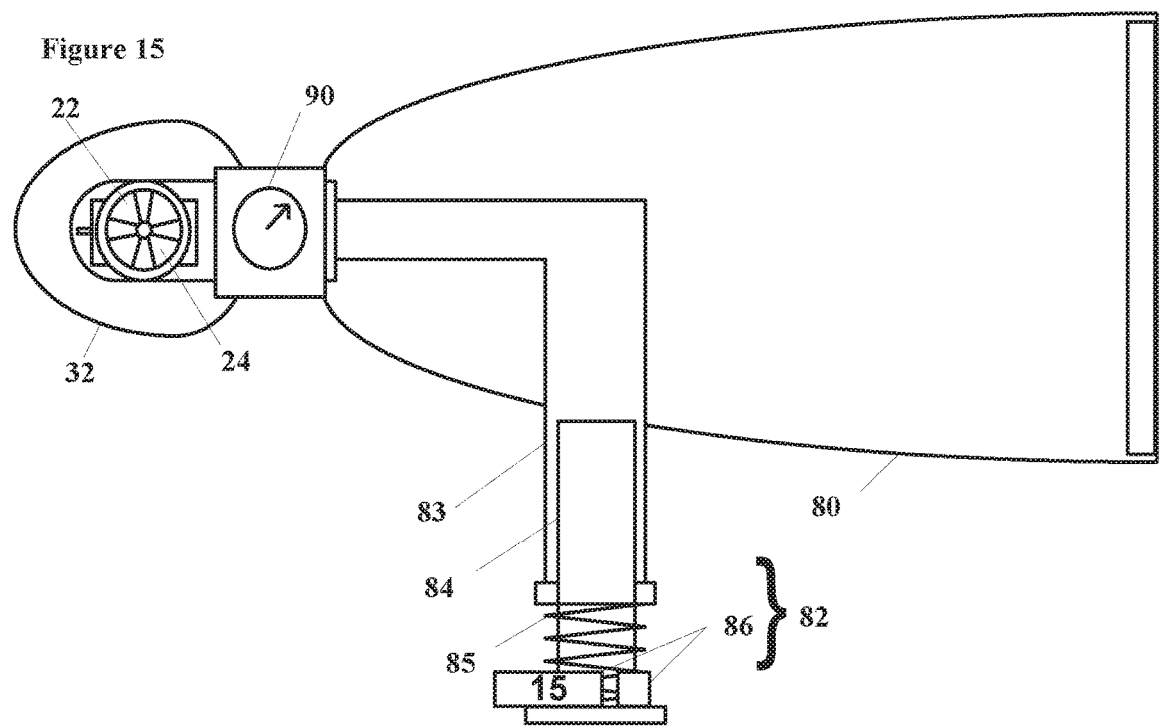
FIG. 15 is a schematic top view of a resuscitation apparatus according to another embodiment, in which a plunger-type mechanism is used to transfer volume to a face mask.

In FIG. 15 a top view schematic is shown describing an alternative resuscitation apparatus which includes a rigid or semi-rigid plunger-type mechanism instead of a dual bag or plurality of bags arrangement. In this embodiment the apparatus includes a holder 80, again ergonomically configured for grasping with one hand, and a plunger-type mechanism 82, the combination configured to enable proper biomechanics to operate. The plunger mechanism includes a barrel 83, plunger 84, and spring 85. The plunger 84 is depressed, typically with the thumb, into the barrel 83 to displace volume from the barrel into the manifold and ultimately out of the face mask. The spring causes the plunger to return to its resting position, which draws ambient air in through the inlet ports 24 of the refill valve 22 as previously described. A spacer array 86 may be used to control the stroke distance of the plunger, for example, a 15 ml spacer if selected would allow the plunger to displace 15 ml of volume when fully depressed. Other volume spacers may be selected to deliver other volumes. While a plunger type mechanism is described in this embodiment as an exemplary positive volume displacement mechanism, other volume displacement mechanisms can be used, and for brevity are not all listed and shown in the figures. Alternatively, as also illustrated in FIG. 15, a volume delivery gauge 90 that is in-line with the airflow channel in the manifold can be provided to measure the amount of volume delivered. The gauge may be a rotimeter, which integrates the amount of flow being delivered by an inspiratory stroke, and displays the integrated amount as a volume. The gauge may automatically reset by the use of atmospheric valving when flow is reversed during the exhalation cycle when the bag or plunger mechanism recoils with fresh air drawn in through the refill valve 22. Although delivery gauge 90 is shown in the embodiment of FIG. 15, delivery gauge 90 can be used in any of the embodiments described herein. As an alternative to or in addition to a volume gage in line with the ventilation gas flow, a pressure gage can be used to indicate to the user the amount of pressure being generated by the system.

Referring to FIG. 16, an alternative embodiment of a resuscitation apparatus is shown. Here an outer compressible structure 200 is mechanically coupled with couplers 204 to a compressible inner structure 202. Compression of outer compressible structure 200 by the user squeezing it with one hand is ergonomically permitted due to the size, shape, and compliance of the outer structure 200. The squeezing motion uses proper biomechanics. When the outer structure 200 is squeezed, mechanical couplers 204 act to in turn compress the inner structure, here ventilation bellows 202, which expels its volume V through the connecting tube 206 through the gas manifold assembly 210 and through the face mask 32. In this embodiment, since compression of the ventilation bellows 202 is by mechanical coupling and not by surrounding pressure increase, the outer compressible structure 200 need not be sealed and has an endcap 206 that may be open to atmosphere with a vent port 208.

Manual ventilation by the resuscitation apparatuses and method described herein can be performed based on delivery of a particular volume, in which case the resultant lung pressure can be determined by lung compliance and resistance, as well as frequency related parameters in the delivery cycle. Or, manual ventilation can be performed based on delivery of a particular pressure, in which case the amount of volume delivered to the lung is determined by the lung compliance and resistance. In some embodiments, both types of manual ventilation are used; either delivery of a known prescribed volume, or delivery of a known prescribed pressure.

It should be noted that while the features and functional elements described throughout are often provided in the context of infant manual emergency bag/mask ventilation, the same principles may apply to other applications, such as non-emergency ventilation using a bag (such as medication delivery) as well as non-infant applications. In the latter case, while there may not be a dire unmet need in non-infant emergency bag/mask ventilation that there is in infant resuscitation, training, equipment, and technique are still factors to consider, and new apparatuses and methods, as described herein, would provide an improvement over the state of the art, even for adult resuscitation. The disclosed resuscitation apparatuses therefore contemplate a range of volume sizes, from a premature infant requiring 5 ml of ventilation volume to be delivered, up to a large adult requiring over 500 ml of ventilation volume to be delivered. Specific size options of the apparatus are contemplated, such as premature infant, term infant, baby, pediatric, small adult, medium adult, and large adult, each size option itself optionally including a range of volumes to be selected based on the requirements of the patient within that age category. While a face mask has been used as an exemplary patient interface, other patient interfaces are contemplated, such as nasal cannula and airway tubes.

The invention claimed is:

1. An apparatus for respiratory resuscitation of an individual comprising:
an actuator bag having (i) a non-compressed free state first size and compressible to a compressed state second size and (ii) an inside that is pneumatically sealed to not communicate with the outside of the bag;
one or more ventilation bags disposed within the inside of the actuator bag, each one or more ventilation bags having (i) a proximal single opening at a patient end in pneumatic communication with outside ambient air, (ii) other than the single opening a body sealed to the outside, and (iii) a non-compressed free-state first volume corresponding to the actuator bag free state;
a fluidically sealed space between the inside of the actuator bag and the outside of the ventilation bags;
and further wherein (a) compression of the actuator bag from its non-compressed free state first size to its compressed state second size increases its internal pressure in the fluidically sealed space without allowing any gas to escape out of the fluidically sealed space to compress the one or more ventilation bags to it's compressed-state second volume to displace gas in the bag to deliver a volume of breath to the individual through only the ventilation bags' single opening at the patient end, and (b) discontinuation of the compression force on the actuator bag allows the actuator bag to naturally expand to its resting state, causing the fluidically sealed space to return to its free state thereby causing the ventilation bags to expand to the free state volume, thereby refilling the ventilation bags with gas entering through the single opening at the patient end with a gas volume available for a next breath delivery.

2. The apparatus of claim 1, further comprising a face mask coupled to the single opening at the patient end of the one or more ventilation bags.

3. The apparatus of claim 1, wherein the one or more ventilation bags has a bellows shape, which contracts and expands in a geometrically controlled axial direction, or an oval or a spherical shape which when compressed compresses radially for substantially its entire length.

4. The apparatus of claim 1, wherein the one or more ventilation bags has a bellows shape which when compressed compresses in a geometrically controlled axial direction.

5. The apparatus of claim 1, wherein the actuator bag is transparent in order to visualize the ventilation bag changing from its free state to its compressed state.

6. The apparatus of claim 1, wherein the inside volume of a ventilation bag is the breathing volume of a newborn term infant and less than 50 ml.

7. The apparatus of claim 1, wherein the volume of gas drawn into the ventilation bags through the single opening at the patient end during recovery of the ventilation bags from the compressed state to the free state comprises ambient air.

8. The apparatus of claim 1, further comprising an air inlet port configured to attach a source of oxygen to the single opening at the patient end of the one or more ventilation bags.

9. The apparatus of claim 1, wherein the volume of gas drawn into the ventilation bags through the single opening at the patient end during recovery of the ventilation bags from the compressed state to the free state comprises oxygen enriched air.

10. The apparatus of claim 1 further comprising a volume adjustment mechanism, wherein the volume adjustment mechanism is configured to select a volume of breath for delivery to the individual, wherein the volume settings are at least two settings between 10 ml and 50 ml and wherein each setting is set and determined by the internal volume of the one or more ventilation bags.

* * * * *